United States Patent
Inoue et al.

(10) Patent No.: US 8,165,370 B2
(45) Date of Patent: Apr. 24, 2012

(54) MEDICAL IMAGE PROCESSING APPARATUS AND MEDICAL IMAGE PROCESSING METHOD

(75) Inventors: Ryoko Inoue, Hachioji (JP); Hirokazu Nishimura, Hachioji (JP); Hideki Tanaka, Tama (JP); Kenji Nakamura, Chiba (JP); Miho Sawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 579 days.

(21) Appl. No.: 12/359,719

(22) Filed: Jan. 26, 2009

(65) Prior Publication Data

US 2009/0148017 A1    Jun. 11, 2009

Related U.S. Application Data

(63) Continuation of application No. PCT/JP2007/057922, filed on Apr. 10, 2007.

(30) Foreign Application Priority Data

Jul. 27, 2006   (JP) ................................ 2006-205142

(51) Int. Cl.
*G06K 9/00*    (2006.01)

(52) U.S. Cl. ......... 382/128; 382/131; 382/154; 382/190

(58) Field of Classification Search .................. 382/128, 382/190, 154, 131
See application file for complete search history.

(56) References Cited

U.S. PATENT DOCUMENTS

| 2002/0164061 A1* | 11/2002 | Paik et al. ..................... 382/131 |
| 2002/0193687 A1* | 12/2002 | Vining et al. ................. 600/425 |
| 2003/0223627 A1* | 12/2003 | Yoshida et al. ............... 382/128 |
| 2006/0221074 A1* | 10/2006 | Matsumoto ................... 345/424 |

FOREIGN PATENT DOCUMENTS

| JP | 2004-097535 | 4/2004 |
| JP | 2005-192880 | 7/2005 |
| JP | 2006-187470 | 7/2006 |
| WO | WO 2006/070669 A1 | 7/2006 |

OTHER PUBLICATIONS

Kimura et al., "A study on automated detection of colonic polyps from 3D abdominal CT images based on shape", Institute of Electronics, Information and Communication Engineers of Japan, IEICE Technical Report (MI2003-102), 2004, pp. 29-34.
Hiroyuki Yoshida, et al., "Computer-aided Diagnosis Scheme for Detection of Polyps at CT Colonography", Radio Graphics, Jul. 2002, vol. 22 No. 4, pp. 963-979.

* cited by examiner

*Primary Examiner* — Joseph Chang
*Assistant Examiner* — Jeffrey Shin
(74) *Attorney, Agent, or Firm* — Scully, Scott, Murphy & Presser, P.C.

(57) ABSTRACT

Main parts of an endoscope system of the present invention include a medical observation apparatus, a medical image processing apparatus, and a monitor. A CPU of the medical image processing apparatus is constituted by function units including a three-dimensional model estimating unit, a detection target area setting unit, a shape feature value calculating unit, a three-dimensional shape detecting unit, a threshold determining unit, and a polyp determining unit. Such a configuration enables to execute a process appropriately adapted to an observation state of a targeted two-dimensional image and to improve the detection accuracy in the detection of a lesion with locally elevated shape as compared to the past.

12 Claims, 13 Drawing Sheets

| Z COORDINATE | T1 | T2 |
|---|---|---|
| 0 ~ 10 | 0.90 | 0.15 |
| 10 ~ 20 | 0.90 | 0.14 |
| 20 ~ 30 | 0.91 | 0.13 |
| ⋮ | ⋮ | ⋮ |
| 50 ~ | 0.95 | 0.10 |

| THE NUMBER OF DATA POINTS | T1 | T2 |
|---|---|---|
| 0 ~ 8 | 0.0 | 0.0 |
| 9 ~ 13 | 0.90 | 0.14 |
| 14 ~ 18 | 0.91 | 0.13 |
| ⋮ | ⋮ | ⋮ |
| 29 ~ | 0.95 | 0.10 |

MEDICAL IMAGE PROCESSING APPARATUS AND MEDICAL IMAGE PROCESSING METHOD

CROSS REFERENCE TO RELATED APPLICATION

This application is a continuation application of PCT/JP2007/057922 filed on Apr. 10, 2007 and claims benefit of Japanese Application No. 2006-205142 filed in Japan on Jul. 27, 2006, the entire contents of which are incorporated herein by this reference.

BACKGROUND OF INVENTION

1. Field of the Invention

The present invention relates to a medical image processing apparatus and a medical image processing method, and more particularly, to a medical image processing apparatus and a medical image processing method that estimate a three-dimensional model of a living tissue based on a two-dimensional image of an image of the living tissue.

2. Description of the Related Art

Conventionally, observations have been generally performed in the medical field using image pickup apparatuses such as an X-ray diagnostic apparatus, a CT, an MRI, an ultrasound observation apparatus, and an endoscope apparatus. Among the image pickup apparatuses, the endoscope apparatus includes, for example, an insertion portion that can be inserted into the body cavity. Image pickup means such as a solid image pickup device picks up an image in the body cavity formed by an objective optical system arranged at a distal end portion of the insertion portion and outputs the image as an image pickup signal, and a graphical image of the image in the body cavity is displayed on displaying means such as a monitor based on the image pickup signal. The endoscope apparatus is operated and configured this way. The user observes an organ or the like in the body cavity based on the graphical image of the image in the body cavity displayed on the displaying means such as a monitor.

The endoscope apparatus can directly pick up an image of digestive tract mucosa. Therefore, the user can comprehensively observe, for example, color tone of mucosa, shape of lesion, and microstructure of mucosal surface.

The endoscope apparatus can also detect an image including a lesion site such as a polyp by using an image processing method, such as an image processing method described in Japanese Patent Application Laid-Open Publication No. 2005-192880 (conventional document 1), capable of detecting a predetermined image in which a lesion with locally elevated shape exists.

The image processing method described in the conventional document 1 can extract the contour of an inputted image and detect a lesion with locally elevated shape in the image based on the shape of the contour.

Conventionally, in a colonic polyp detection process, three-dimensional data is estimated from a two-dimensional image, and three-dimensional feature values (Shape Index/Curvedness) are used to detect colonic polyps (conventional document 2: Institute of Electronics, Information and Communication Engineers of Japan, IEIC Technical Report (MI2003-102), A study on automated detection of colonic polyps from 3D abdominal CT images based on shape information, Kimura, Hayashi, Kitasaka, Mori, Suenaga, pp. 29 to 34, 2004). The three-dimensional feature values are realized by calculating partial differential coefficients in a reference point based on three-dimensional data and using the partial differential coefficients. In the colonic polyp detection process, possible polyps are detected by applying a threshold process to the three-dimensional feature values.

SUMMARY OF THE INVENTION

A medical image processing apparatus of one aspect of the present invention is constituted by including:

a three-dimensional model estimating unit for estimating a three-dimensional model of a living tissue based on a two-dimensional image of an image of the living tissue in a body cavity, the two-dimensional image inputted from a medical image pickup apparatus;

a detection target area setting unit for setting a detection target area of a lesion with elevated shape in the three-dimensional model;

a shape feature value calculating unit for calculating shape feature values indicative of a state of the shape at each data point included in the detection target area;

a three-dimensional shape detecting unit for detecting a lesion area with locally elevated shape existing in the detection target area based on a threshold process with respect to the shape feature values; and a threshold determining unit for determining thresholds applied in the three-dimensional shape detecting unit.

A medical image processing method of one aspect of the present invention is constituted by including:

a three-dimensional model estimating step for estimating a three-dimensional model of a living tissue based on a two-dimensional image of an image of the living tissue in a body cavity, the two-dimensional image inputted from a medical image pickup apparatus;

a detection target area setting step for setting a detection target area of a lesion with elevated shape in the three-dimensional model;

a shape feature value calculating step for calculating shape feature values indicative of a state of the shape at each data point included in the detection target area;

a three-dimensional shape detecting step for detecting a lesion area with locally elevated shape existing in the detection target area based on a threshold process with respect to the shape feature values; and a threshold determining step for determining thresholds applied in the three-dimensional shape detecting step.

DETAILED DESCRIPTION OF THE PREFERRED EMBODIMENT(S)

Embodiments of the present invention will now be described with reference to the drawings.

(First Embodiment)

Figure 1:
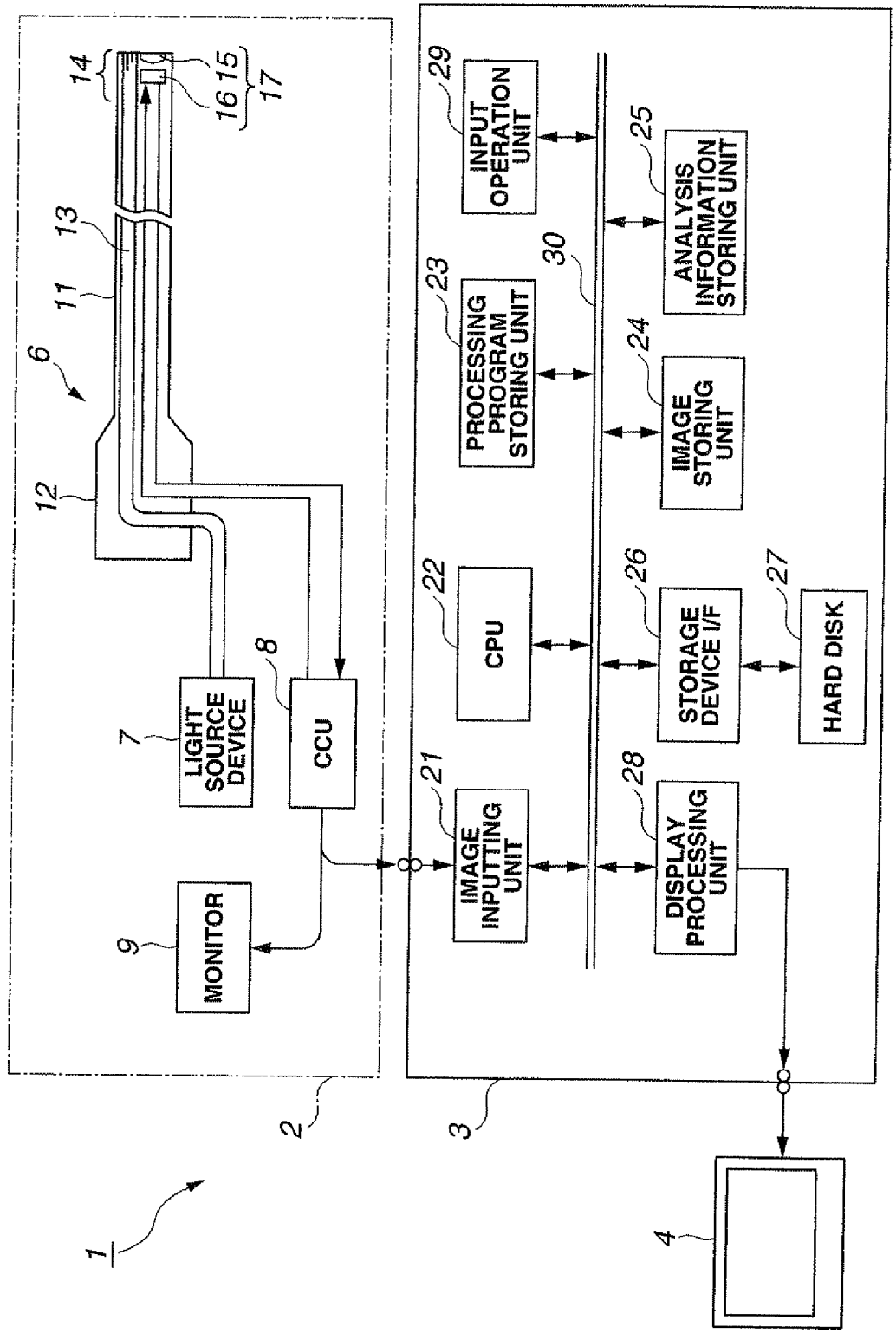
FIG. 1 is a diagram showing an example of an overall configuration of an endoscope system in which a medical image processing apparatus according to a first embodiment of the present invention is used.
Figure 2:
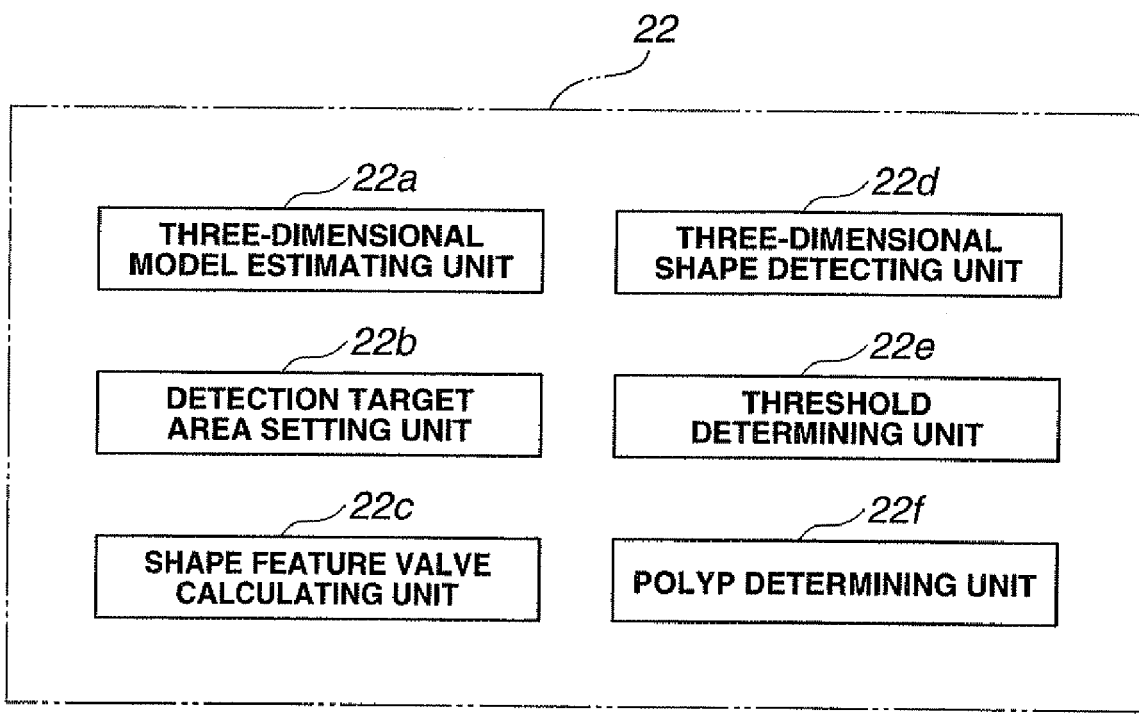
FIG. 2 is a functional block diagram showing a functional configuration of a CPU of FIG. 1.
Figure 3:
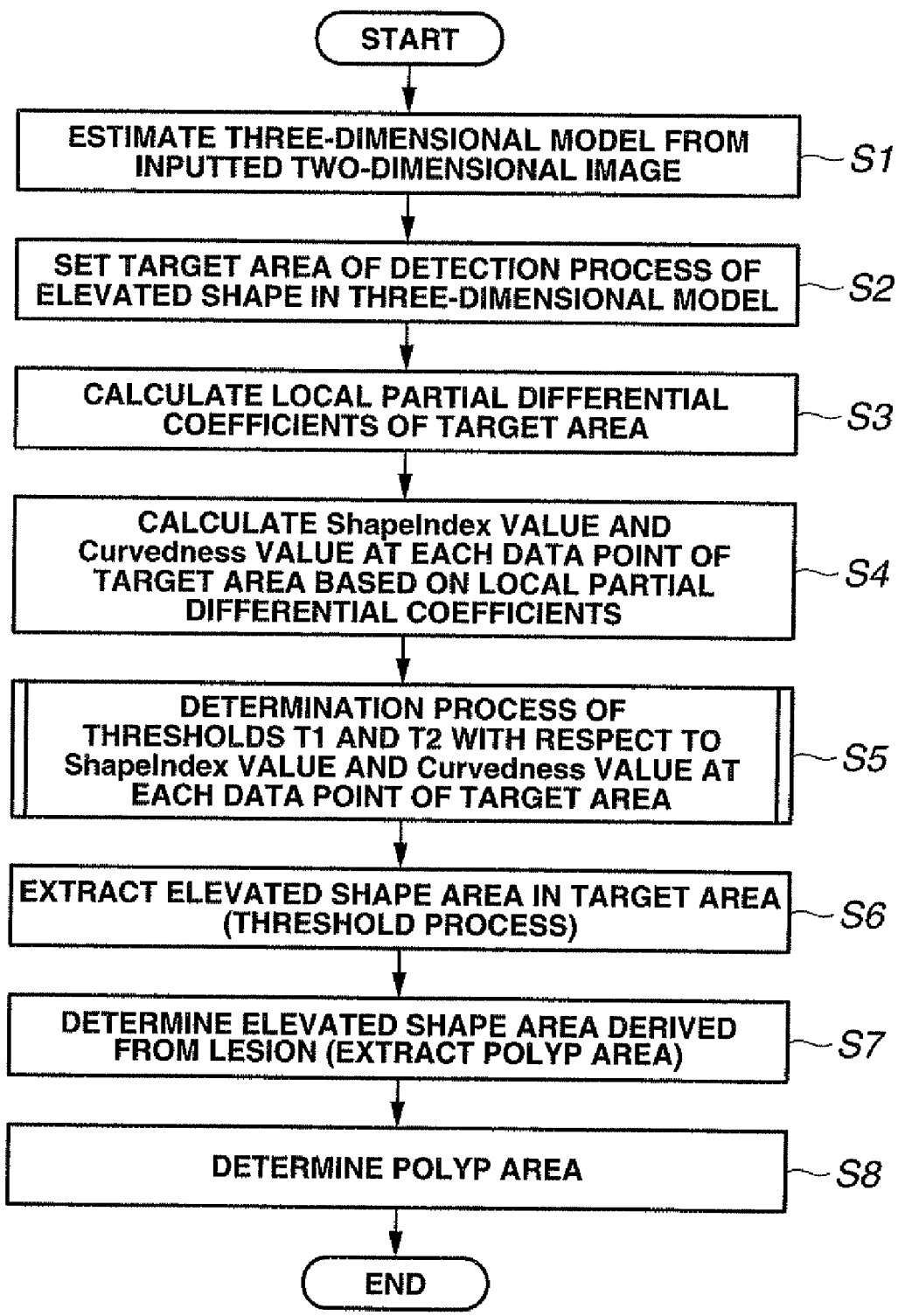
FIG. 3 is a flow chart showing a flow of a process of the CPU of FIG. 2.
Figures 4, 5:
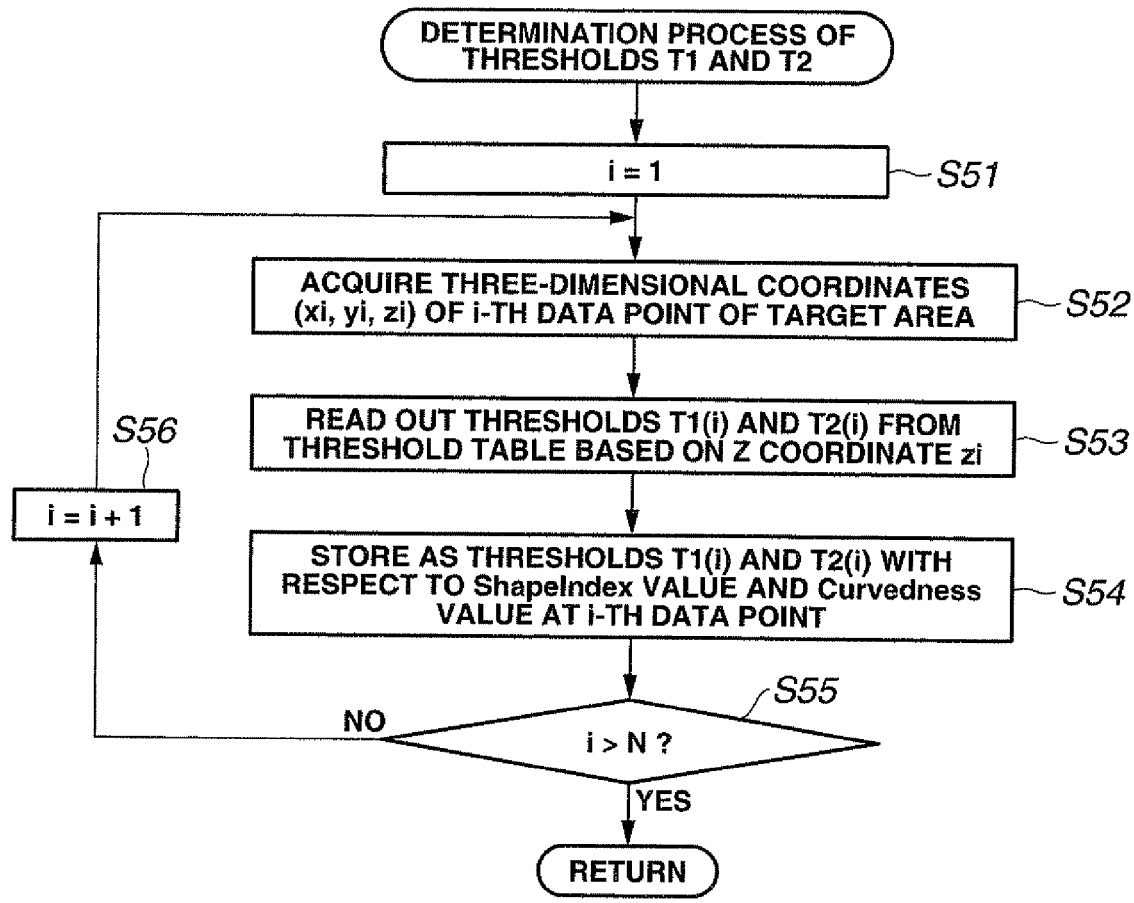
FIG. 4 is a flow chart showing a flow of a determination process of thresholds T1 and T2 of FIG. 3.
FIG. 5 is a diagram showing "Z coordinate-thresholds T1, T2" threshold table data used in the process of FIG. 4.
Figure 6:
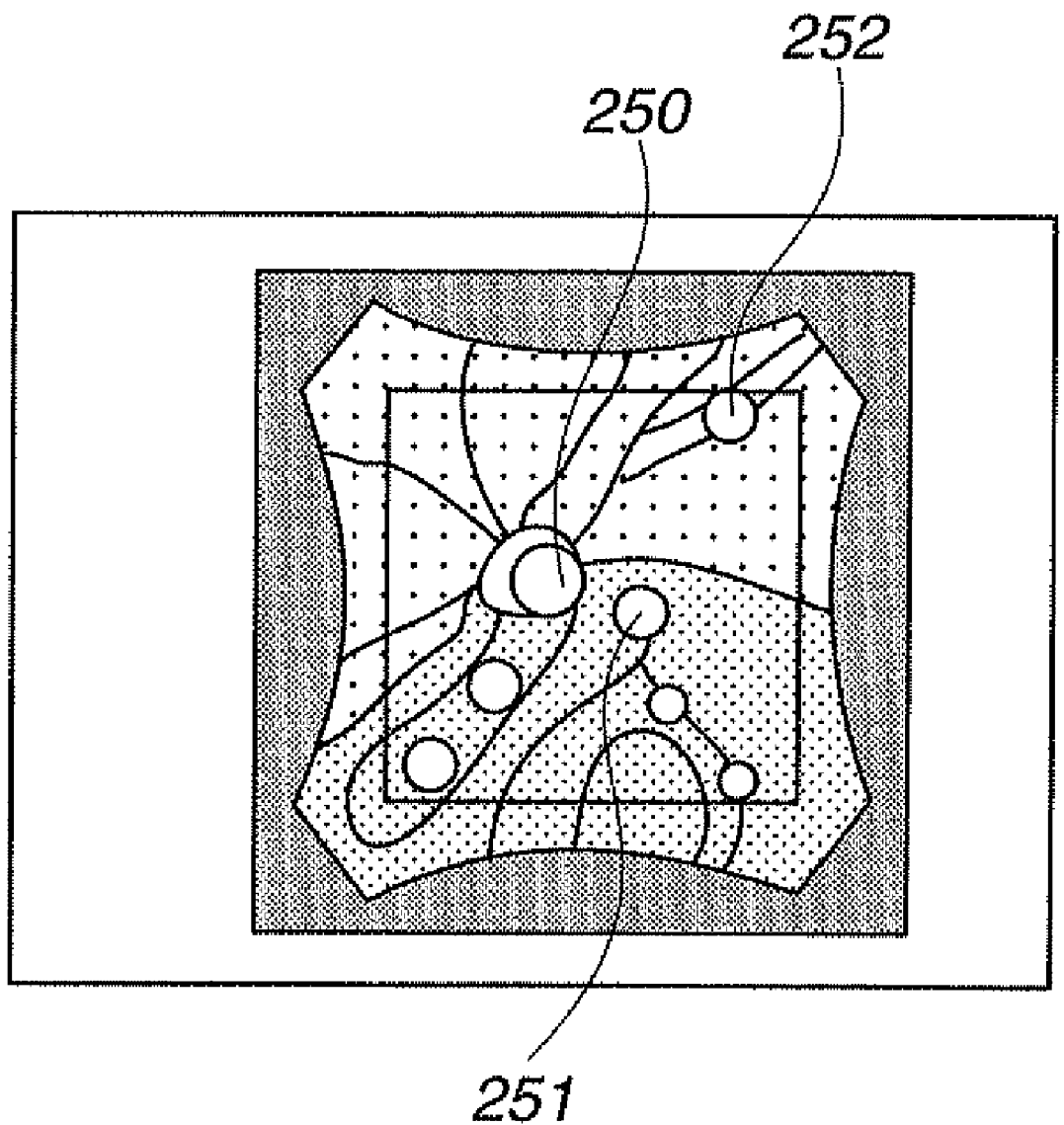
FIG. 6 is a diagram for explaining the process of FIG. 4.

FIGS. 1 to 6 relate to a first embodiment of the present invention. FIG. 1 is a diagram showing an example of an overall configuration of an endoscope system in which a medical image processing apparatus is used. FIG. 2 is a functional block diagram showing a functional configuration of a CPU of FIG. 1. FIG. 3 is a flow chart showing a flow of a process of the CPU of FIG. 2. FIG. 4 is a flow chart showing a flow of a determination process of thresholds T1 and T2 of FIG. 3. FIG. 5 is a diagram showing "Z coordinate-thresholds T1, T2" threshold table data used in the process of FIG. 4. FIG. 6 is a diagram for explaining the process of FIG. 4.

As shown in FIG. 1, main parts of the endoscope system 1 of the present embodiment include a medical observation apparatus 2, a medical image processing apparatus 3, and a monitor 4.

The medical observation apparatus 2 is an observation apparatus that picks up an image of a subject and that outputs a two-dimensional image of the image of the subject. The medical image processing apparatus 3 is an image processing apparatus that is configured by a personal computer and the like, processes a video signal of the two-dimensional image outputted from the medical observation apparatus 2, and outputs the processed video signal as an image signal. The monitor 4 is a display apparatus that displays an image based on the image signal outputted from the medical image processing apparatus 3.

Main parts of the medical observation apparatus 2 include an endoscope 6, a light source device 7, a camera control unit (hereinafter, abbreviated as "CCU") 8, and a monitor 9.

The endoscope 6 is inserted into a body cavity of a subject to be examined, picks up an image of a subject such as a living tissue existing in the body cavity, and outputs the image as an image pickup signal. The light source device 7 supplies illumination light for illuminating the subject picked up by the endoscope 6. The CCU 8 performs various controls to the endoscope 6, processes the image pickup signal outputted from the endoscope 6, and outputs the signal as a video signal of a two-dimensional image. The monitor 9 displays the image of the subject picked up by the endoscope 6 based on the video signal of the two-dimensional image outputted from the CCU 8.

The endoscope 6 includes an insertion portion 11 inserted into the body cavity and an operation portion 12 arranged on the proximal end side of the insertion portion 11. From the proximal end side of the insertion portion 11 to a distal end portion 14 on the distal end side of the insertion portion 11, a light guide 13 for transmitting the illumination light supplied from the light source device 7 is inserted.

The distal end side of the light guide 13 is arranged at the distal end portion 14 of the endoscope 6, and the posterior end is connected to the light source device 7.

Since the light guide 13 is configured this way, the illumination light supplied from the light source device 7 is transmitted by the light guide 13 and then emitted from an illumination window not shown that is arranged on the distal end surface of the distal end portion 14 of the insertion portion 11. As the illumination light is emitted from the illumination window not shown, a living tissue or the like as a subject is illuminated.

Arranged at the distal end portion 14 of the endoscope 6 is an image pickup unit 17 including an objective optical system 15 attached to an observation window not shown adjacent to the illumination window not shown and an image pickup device 16 that is arranged at an imaging position of the objective optical system 15 and that is constituted by, for example, a CCD (Charge Coupled Device). According to the configuration, an image of the subject formed by the objective optical system 15 is picked up by the image pickup device 16 and then outputted as an image pickup signal. The constituent of the image pickup device 16 is not limited to the CCD, but may also be constituted by a C-MOS sensor.

The image pickup device 16 is connected to the CCU 8 through a signal line. The image pickup device 16 is driven based on a drive signal outputted from the CCU 8 and outputs, to the CCU 8, an image pickup signal corresponding to the picked up image of the subject.

As a result of signal processing by a signal processing circuit not shown arranged inside the CCU 8, the image pickup signal inputted to the CCU 8 is converted and outputted as a video signal of a two-dimensional image. The video signal of the two-dimensional image outputted from the CCU 8 is outputted to the monitor 9 and the medical image processing apparatus 3. Consequently, the monitor 9 displays the image of the subject as a two-dimensional image, based on the video signal outputted from the CCU 8.

The medical image processing apparatus 3 includes: an image inputting unit 21 that applies an A/D conversion to the video signal of the two-dimensional image outputted from the medical observation apparatus 2 and then outputs the signal; a CPU 22 as a central processing unit that performs image processing to the video signal outputted from the image inputting unit 21; a processing program storing unit 23 that stores a processing program related to the image processing; an image storing unit 24 that stores the video signal and the like outputted from the image inputting unit 21; and an analysis information storing unit 25 that stores a calculation result and the like of the image processing performed by the CPU 22.

The medical image processing apparatus 3 includes: a storage device interface (I/F) 26; a hard disk 27 as a storage device that stores image data as an image processing result of the CPU 22, various data used by the CPU 22 in the image processing, and the like through the storage device I/F 26; a display processing unit 28 that performs display processing for displaying, on the monitor 4, image data based on the image data as an image processing result of the CPU 22 and that outputs the image data after the display processing as an image signal; and an input operation unit 29 that allows a user to input parameters in the image processing by the CPU 22 and an operation instruction to the medical image processing apparatus 3 and that is constituted by a pointing device or the like such as a keyboard and a mouse. The monitor 4 displays an image based on the image signal outputted from the display processing unit 28.

The image inputting unit 21, the CPU 22, the processing program storing unit 23, the image storing unit 24, the analysis information storing unit 25, the storage device interface 26, the display processing unit 28, and the input operation unit 29 of the medical image processing apparatus 3 are interconnected through a data bus 30.

As shown in FIG. 2, the CPU 22 is constituted by function units including a three-dimensional model estimating unit 22a as three-dimensional model estimating means, a detection target area setting unit 22b as detection target area setting means, a shape feature value calculating unit 22c as shape feature value calculating means, a three-dimensional shape detecting unit 22d as three-dimensional shape detecting means, a threshold determining unit 22e as threshold determining means, and a polyp determining unit 22f.

Software executed by the CPU 22 realizes the function units in the present embodiment. Detailed operations of the function units will be described below.

An operation of the endoscope system 1 of the present embodiment configured this way will be described using flow charts of FIGS. 3 and 4 and with reference to FIGS. 5 and 6.

After applying power to the components included in the endoscope system 1, the user inserts the insertion portion 11 of the endoscope 6 into the body cavity of the subject to be examined.

Once the user inserts the insertion portion 11 into the body cavity of the subject to be examined, the image pickup unit 17 arranged at the distal end portion 14 picks up an image of the subject such as a living tissue existing in the body cavity. The image of the subject picked up by the image pickup unit 17 is outputted to the CCU 8 as an image pickup signal.

The CCU 8 processes, in a signal processing circuit not shown, the image pickup signal outputted from the image pickup device 16 of the image pickup unit 17 to convert and output the image pickup signal as a video signal of a two-dimensional image. Based on the video signal outputted from the CCU 8, the monitor 9 displays the image of the subject picked up by the image pickup unit 17 as a two-dimensional image. The CCU 8 outputs, to the medical image processing apparatus 3, the video signal of the two-dimensional image obtained by processing the image pickup signal outputted from the image pickup device 16 of the image pickup unit 17.

The video signal of the two-dimensional image outputted to the medical image processing apparatus 3 is applied with an A/D conversion in the image inputting unit 21 and then inputted to the CPU 22.

As shown in FIG. 3, the three-dimensional model estimating unit 22a of the CPU 22 uses, for example, a "Shape From Shading" method to apply, to the two-dimensional image outputted from the image inputting unit 21 in step S1, a process such as a geometric conversion based on luminance information or the like of the two-dimensional image to thereby estimate a three-dimensional model according to the two-dimensional image and then stores coordinates of each data point of the three-dimensional model in the hard disk 27 through the storage device I/F 26.

In step S2, the detection target area setting unit 22b of the CPU 22 detects a change in color tone of the two-dimensional image outputted from the image inputting unit 21 and a change in elevation of the three-dimensional model estimated in the process of step S1 of FIG. 3 to thereby set a target area of the detection target area as an area to be applied with a process of detecting a lesion with elevated shape in the three-dimensional model.

Specifically, for example, after separating the two-dimensional image outputted from the image inputting unit 21 into plane images of R (red) image, G (green) image, and B (blue) image, the detection target area setting unit 22b of the CPU 22 detects a change in elevation based on the data of the three-dimensional model estimated according to the R image and detects a change in color tone based on the chromaticity of the R image and the G image. Based on the detection result of the change in elevation and the detection result of the change in color tone, the detection target area setting unit 22b of the CPU 22 sets an area, where both of the change in elevation and the change in color tone are detected, as the target area.

Subsequently, the shape feature value calculating unit 22c of the CPU 22 calculates local partial differential coefficients of the target area in step S3. Specifically, the shape feature value calculating unit 22c of the CPU 22 calculates, with respect to the calculated three-dimensional shape, first-order partial differential coefficients fx, fy, and fz and second-order partial differential coefficients fxx, fyy, fzz, fxy, fyz, and fxz in a local area (curved surface) including a targeted three-dimensional position (x, y, z), where R pixel value is f.

In step S4, based on the local partial differential coefficients, the shape feature value calculating unit 22c of the CPU 22 further calculates a Shape Index value and a Curvedness value, as (three-dimensional shaped) shape feature values, of each data point existing in the process target area of three-dimensional model.

That is, the shape feature value calculating unit 22c of the CPU 22 uses the local partial differential coefficients to calculate a Gaussian curvature K and an average curvature H.

Meanwhile, using the Gaussian curvature K and the average curvature H, principal curvatures k1 and k2 (k1≧k2) of the curved surface is expressed as $$k1 = H + (H^2 - K)^{1/2} \quad k2 = H - (H^2 - K)^{1/2} \tag{1}$$

A Shape Index SI and a Curvedness CV as feature values that indicate the curved surface shape in this case are expressed by $$SI = 1/2 - (1/\pi)\arctan[(k1+k2)/(k1-k2)] \tag{2}$$

$$CV = ((k1^2 + k2^2)/2)^{1/2} \tag{3},$$

respectively.

In this way, the shape feature value calculating unit 22c of the CPU 22 calculates, as three-dimensional shape information, the Shape Index SI and the Curvedness CV in each three-dimensional curved surface and stores them in the analysis information storing unit 25.

The Shape Index value is a value for expressing a state of concavity and convexity at each data point included in the three-dimensional model and is expressed as a numeric value within the range of 1 or more and 1 or less. Specifically, the Shape Index value close to 0 in individual data points existing in the three-dimensional model indicates the existence of a concave shape, while the Shape Index value close to 1 indicates the existence of a convex shape.

The Curvedness value is a value for expressing the curvature at each data point included in the three-dimensional model. Specifically, in the individual data points existing in the three-dimensional model, a smaller Curvedness value indicates the existence of a sharply curved surface, while a larger Curvedness value indicates the existence of a slowly curved surface.

In step S5, the threshold determining unit 22e of the CPU 22 performs a determination process of thresholds T1 and T2 for comparison with the values of the Shape Index value and the Curvedness value in the data existing in the target area of the three-dimensional model. The determination process of the thresholds T1 and T2 of step S5 will be described in detail below.

In step S6, the three-dimensional shape detecting unit 22d of the CPU 22 compares the values of the Shape Index value and the Curvedness value with the thresholds T1 and T2 determined by the threshold determining unit 22e at each data point existing in the target area of the three-dimensional model to thereby detect a data group with elevated shape among the data points. Specifically, among the data points existing in the process target area of the three-dimensional model, the CPU 22 detects, as a data group with elevated shape, a plurality of data points in which, for example, the Shape Index value is larger than the threshold T1 and the Curvedness value is larger than the threshold T2.

In step S7, the polyp determining unit 22f of the CPU 22 executes an elevated shape determination process of determining whether each of the plurality of data points detected as a data group with elevated shape in the three-dimensional model is a data point with elevated shape derived from a lesion such as polyp.

Subsequently, in step S8, the polyp determining unit 22f of the CPU 22 determines an area including the data group formed by data points with elevated shape derived from a lesion as a polyp area and detects a polyp that is a lesion area.

The CPU 22 then stores the detection result, for example, in the hard disk 27 of FIG. 1 in association with the endoscopic image of the detection target and displays the detection result on the monitor 4 trough the display processing unit 28, for example, side-by-side with the endoscopic image of the detection target.

As a results the monitor 4 displays a three-dimensional model of the subject such that the user can easily recognize the position where the elevated shape derived from a lesion such as polyp exists.

Next, the determination process of the thresholds T1 and T2 of step S5 described above will be described. As shown in FIG. 4, the threshold determining unit 22e of the CPU 22 sets a parameter i to 1 in step S51 and acquires three-dimensional coordinates (xi, yi, zi) of i-th data point in the target area of the three-dimensional model from the analysis information storing unit 25 in step S52.

In step S53, the threshold determining unit 22e of the CPU 22 reads out, through the storage device I/F 26 and based on the Z coordinate zi, thresholds T1($i$) and T2($i$) from "Z coordinate-thresholds T1, T2" threshold table data as shown in FIG. 5 that is stored in the hard disk 27. In step S54, the threshold determining unit 22e of the CPU 22 stores them as the thresholds T1($i$) and T2($i$) of the Shape Index value and the Curvedness value of i-th data point in the analysis information storing unit 25.

In step S55, the threshold determining unit 22e of the CPU 22 determines whether the parameter i has reached a number N of all data points in the target area of the three-dimensional model, and if not i>N, increments the parameter i in step S56 and returns to step S52. The threshold determining unit 22e of the CPU 22 repeats the processes of above described steps S52 to S56 until the thresholds T1($i$) and T2($i$) are determined at all data points in the target area of the three-dimensional model in step S55.

The relationship between the Z coordinate value and T1, T2 may be formulated by applying a linear function or a quadratic function of values shown in the "Z coordinate-thresholds T1, T2" threshold table (see FIG. 5) and may be obtained by formula calculation.

In the two-dimensional image, scatter light from under the mucosa increases when the light source is close, and the incidence of reflected light (second-order light) of other locations also increases. Since the colon endoscopic image is an image pickup image of an intestinal tract, if the intestinal tract direction is in the image, the part of the image at a far location in the depth direction is picked up as viewing the intestinal tract wall obliquely. Therefore, angular characteristics of the reflected light and the scattered light are different from when the intestinal wall is viewed from the front. Thus, the optimal threshold combination of the Shape Index (index indicative of concavity and convexity) and the Curvedness (index indicative of the sharpness of concavity and convexity) for detecting a possible polyp differs in accordance with the Z coordinate of the threshold determination point. For example, in FIG. 6 showing an example of the possible polyp detection in a same threshold combination, not only an essential polyp 250 in the near side, but also a smooth convex 251 in the far side and a peak-like convex 252 are detected.

As described above, in the present embodiment, since the thresholds are corrected using a location (Z coordinate) at the target point of the three-dimensional data, thresholds, in which the influence of the refection/scattering characteristics of the target and the second-order light to the target are removed, can be used for the polyp detection process, and the detection accuracy of the possible polyp can be improved. Therefore, the improvement of the possible polyp detection rate can be promoted in the colon endoscopy for the user.

(Second Embodiment)

Figures 7, 8:
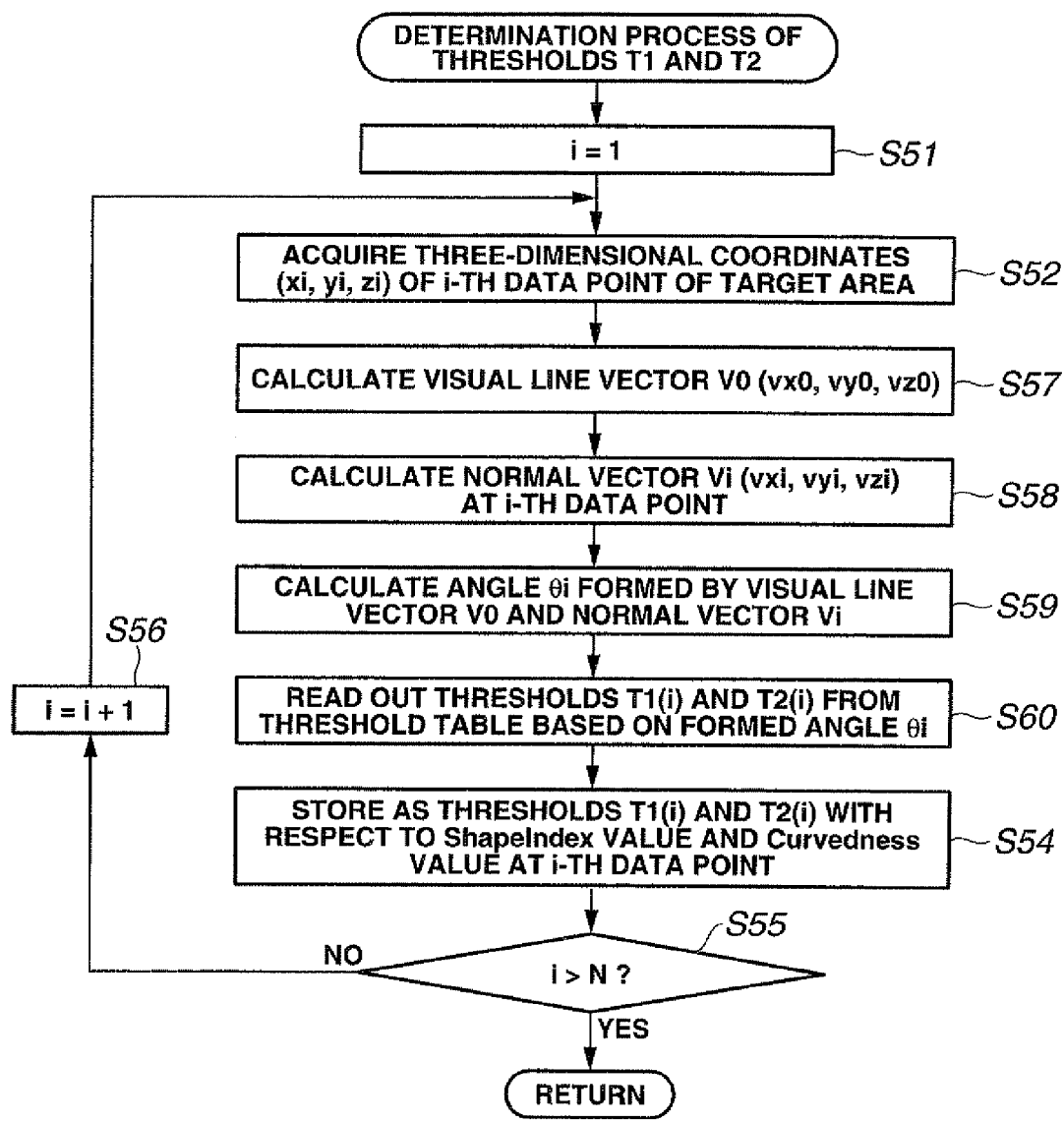
FIG. 7 is a flow chart showing a flow of the determination process of the thresholds T1 and T2 according to a second embodiment of the present invention.
FIG. 8 is a diagram showing "formed angle-multiplication value" threshold table data used in the process of FIG. 7.
Figure 9:
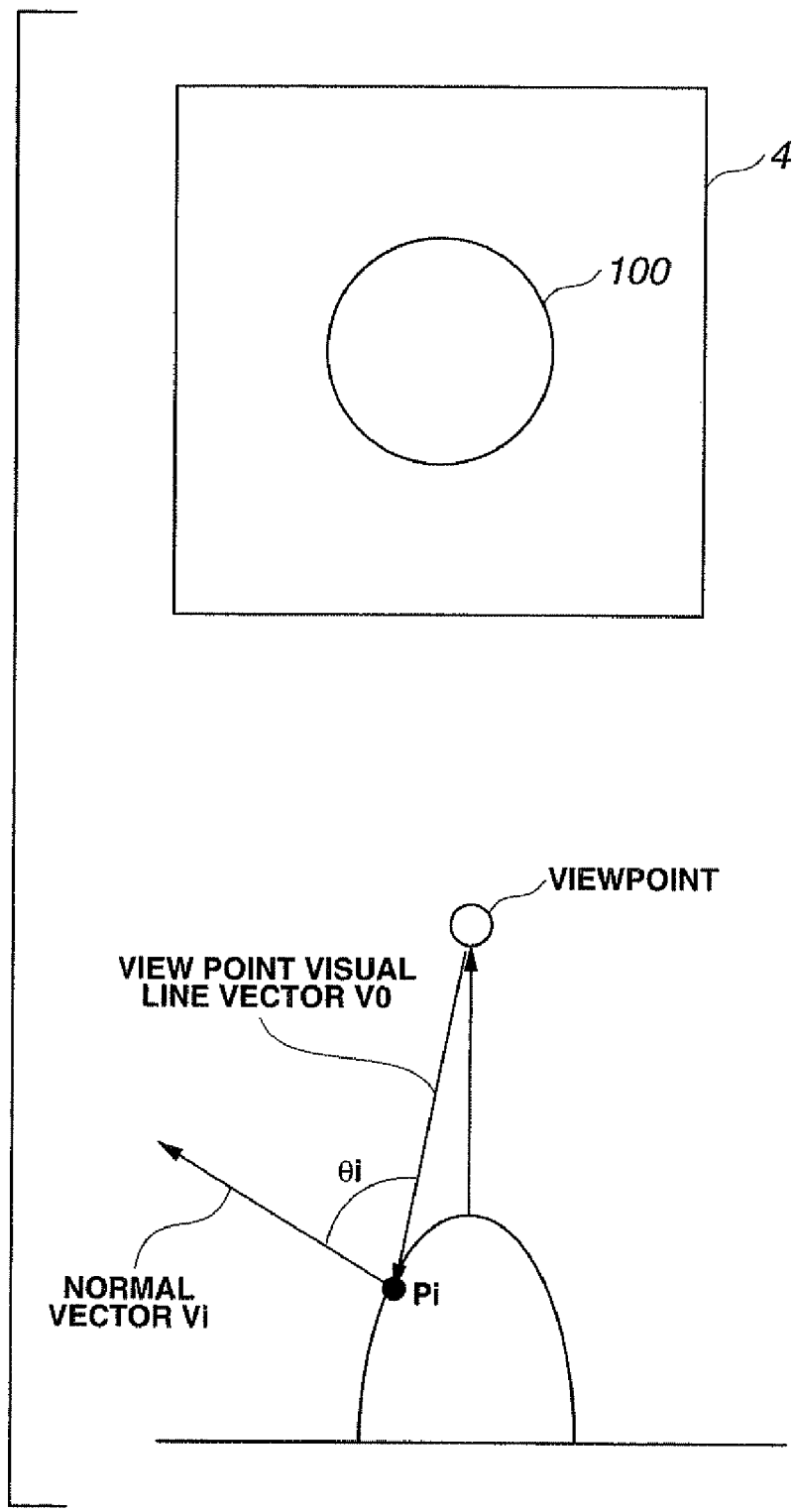
FIG. 9 is a first diagram for explaining the process of FIG. 7.
Figure 10:
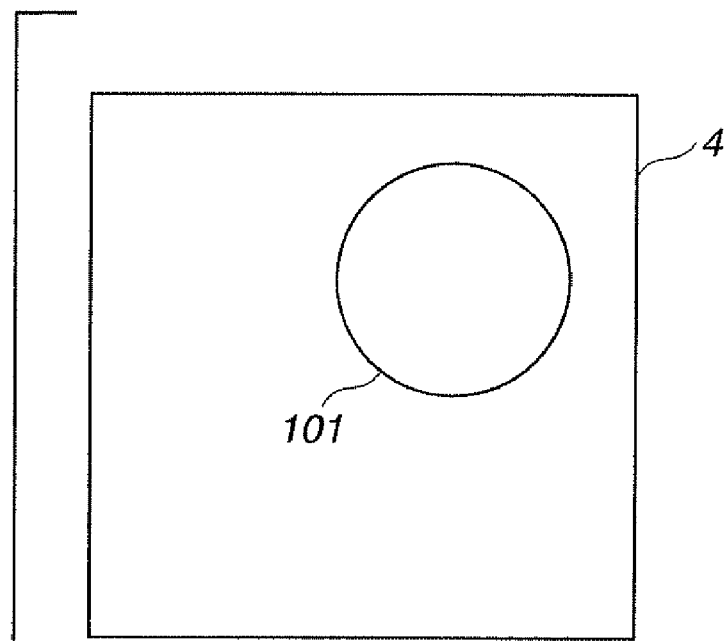
FIG. 10 is a second diagram for explaining the process of FIG. 7.
Figure 10:
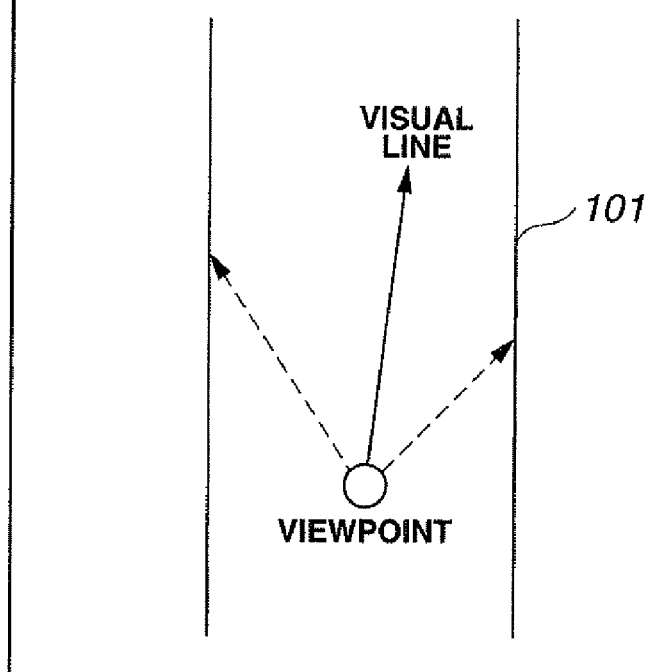
Figure 11:
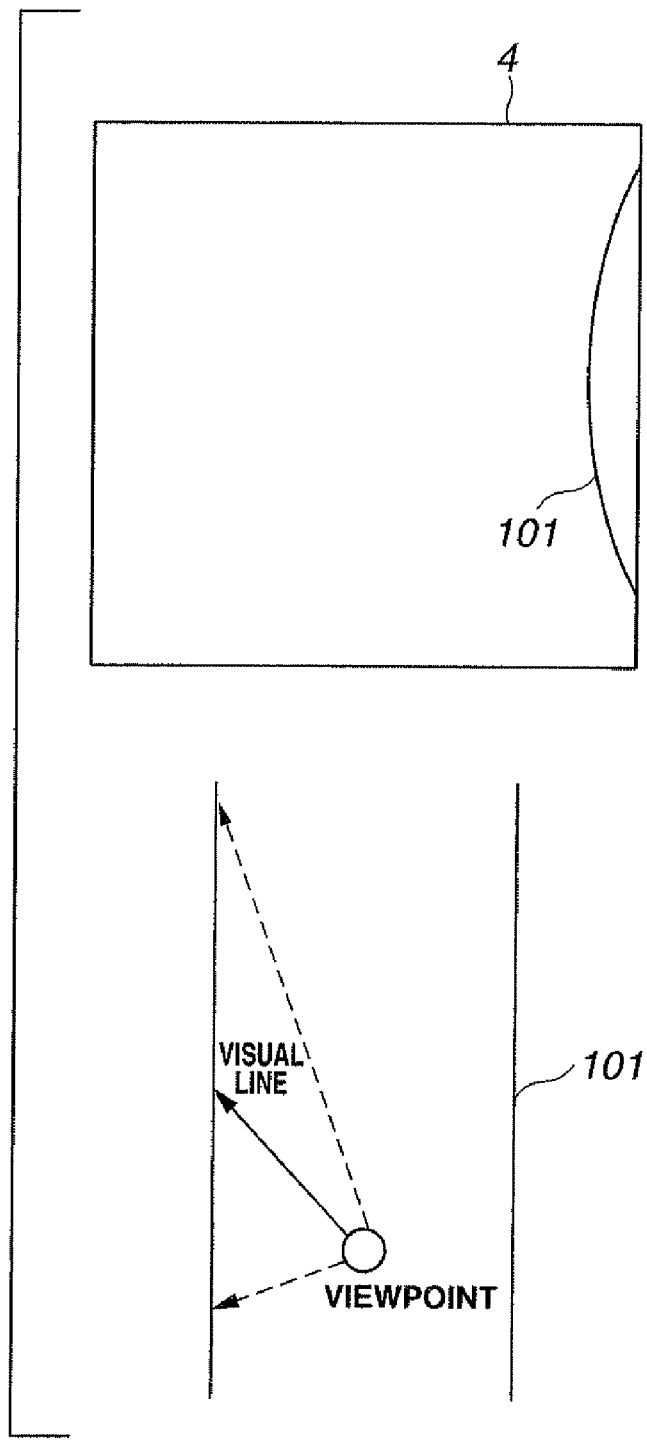
FIG. 11 is a third diagram for explaining the process of FIG. 7.

FIGS. 7 to 11 relate to a second embodiment of the present invention. FIG. 7 is a flow chart showing a flow of the determination process of the thresholds T1 and T2. FIG. 8 is a diagram showing "formed angle-multiplication value" threshold table data used in the process of FIG. 7. FIG. 9 is a first diagram for explaining the process of FIG. 7. FIG. 10 is a second diagram for explaining the process of FIG. 7. FIG. 11 is a third diagram for explaining the process of FIG. 7.

In the second embodiment, the determination process of the thresholds T1 and T2 for comparison with the values of the Shape Index value and the Curvedness value is different from the first embodiment, and the configuration is the same as that of the first embodiment. Therefore, only the different point will be described.

In the determination process of the thresholds T1 and T2 for comparison with the values of the Shape Index value and the Curvedness value of the present embodiment, as shown in FIG. 7, the threshold determining unit 22e of the CPU 22 sets the parameter i to 1 in step S51 and acquires three-dimensional coordinates (xi, yi, zi) of i-th data point in the target area of the three-dimensional model from the analysis information storing unit 25 in step S52.

The threshold determining unit 22e of the CPU 22 then calculates a difference between a viewpoint coordinate and the coordinate point to generate a visual line vector in step S57. The coordinates (x0, y0, z0) of the viewpoint position are determined in step S1 of FIG. 3, and the visual line vector V0 (Vx0, Vy0, Vz0) becomes (xi-x0, yi-y0, zi-z0).

The threshold determining unit 22e of the CPU 22 calculates a normal vector Vi (Vxi, Vyi, Vzi) at the i-th data point in step S58. The normal vector Vi is obtained by calculating differential values (fx, fy, fz) at the data point of the quadric surface f obtained in step S2 of FIG. 3. In step S59, the threshold determining unit 22e of the CPU 22 also calculates an angle θi formed by the visual line vector and the normal vector. The formed angle θi is obtained from an inner product formula of vector.

In the present embodiment, "formed angle-multiplication value" threshold table data as shown in FIG. 8 and default values T1(0) and T2(0) of the thresholds are stored in the hard disk 27.

In step S60, the threshold determining unit 22e of the CPU 22 extracts, from the "formed angle-multiplication value" threshold table data stored in the hard disk 27, multiplication values αi and βi corresponding to the obtained formed angle θi and acquires the default values (T1(0), T2(0)) of the thresholds from the hard disk 27 to obtain values T1(i) (=αi×T1(0)) and T2(i) (=βi×T2(0)) in which the default values T1 and T2 of the thresholds and the multiplication values αi and βi are multiplied respectively.

In step S54, the threshold determining unit 22e of the CPU 22 stores them as the thresholds T1(i) and T2(i) of the Shape Index value and the Curvedness of i-th data point in the analysis information storing unit 25.

In step S55, the threshold determining unit 22e of the CPU 22 determines whether the parameter i has reached the number N of all data points in the target area of the three-dimensional model, and if not i>N, increments the parameter i in step S56 and returns to step S52. The threshold determining unit 22e of the CPU 22 repeats the processes of steps S52, S57 to S60, and S54 to S56 of FIG. 7 described above until the thresholds T1(i) and T2(i) are determined at all data points in the target area of the three-dimensional model in step S55.

Based on the thresholds T1(i) and T2(i), the process, in step S6 shown in FIG. 3, of comparing the values of the Shape Index value and the Curvedness value with the thresholds T1 and T2 determined by the threshold determining unit 22e is executed at each data point existing in the target area of the three-dimensional model.

Since the angular characteristics of the reflected light and the scattered light of the colon endoscopic image differ depending on the front view/oblique view of the intestinal wall, the optimal threshold combination of the Shape Index value and the Curvedness value for the possible polyp detection differs in accordance with the angle formed by the normal vector of the intestinal wall at the threshold determination point and the visual line angle.

For example, FIG. 9 depicts an image of a hemispherical sample 100 picked up as viewed from the front, and there is a problem that the image seen from the viewpoint is elongated to a semi-elliptical shape due to the angular characteristics of the reflected light and the scattered light when the three-dimensional data is generated based on the "Shape From Shading" method.

In the present embodiment, the thresholds are corrected using location and angle information at the target point of the three-dimensional data. Therefore, effects similar to those of the first embodiment can be obtained, and since the table values and the default values are multiplied, optimal thresholds can be obtained in accordance with a change in the default value.

A configuration is possible in which, for example, a lumen detection method in the visual field of the endoscopic image disclosed in Japanese Patent Application Laid-Open Publication No. 2003-93328 is used to determine average thresholds in the entire image based on the existence of the lumen detection in the visual field of the endoscopic image.

If, for example, an entire lumen 101 is detected in the visual field as shown in FIG. 10, the angle formed by the normal vector of the intestinal tract surface and the visual line angle is a large value as an average value of the entire image.

Therefore, for example, a value of formed angle=60 or more of the threshold table of FIG. 8 is used to extract multiplication values αi=1.03 and βi=0.90 to determine the thresholds as T1=1.03×T1(0) and T2=0.90×T2(0).

If the entire lumen 101 is not detected in the visual field as shown in FIG. 11, the angle formed by the normal vector of the intestinal tract surface and the visual line angle is a small value as a threshold with respect to the entire image. Therefore, for example, a value of the formed angle=20 to 30 of the threshold table of FIG. 8 is used to extract multiplication values αi=1.01 and βi=0.98 to determine the thresholds as T1=1.01×T1(0) and T2=0.98×T2(0).

(Third Embodiment)

Figure 12:
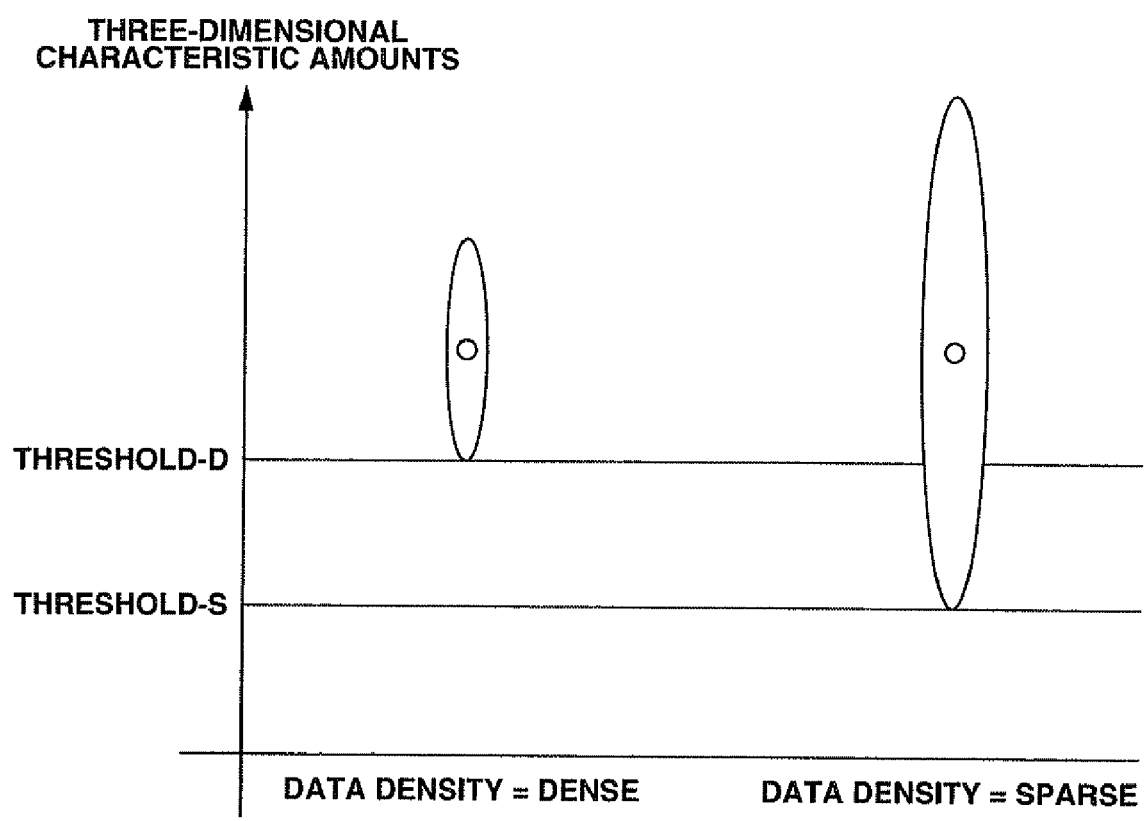
FIG. 12 is a diagram for explaining a calculation process of the local partial differential coefficients according to a third embodiment of the present invention.
Figure 13:
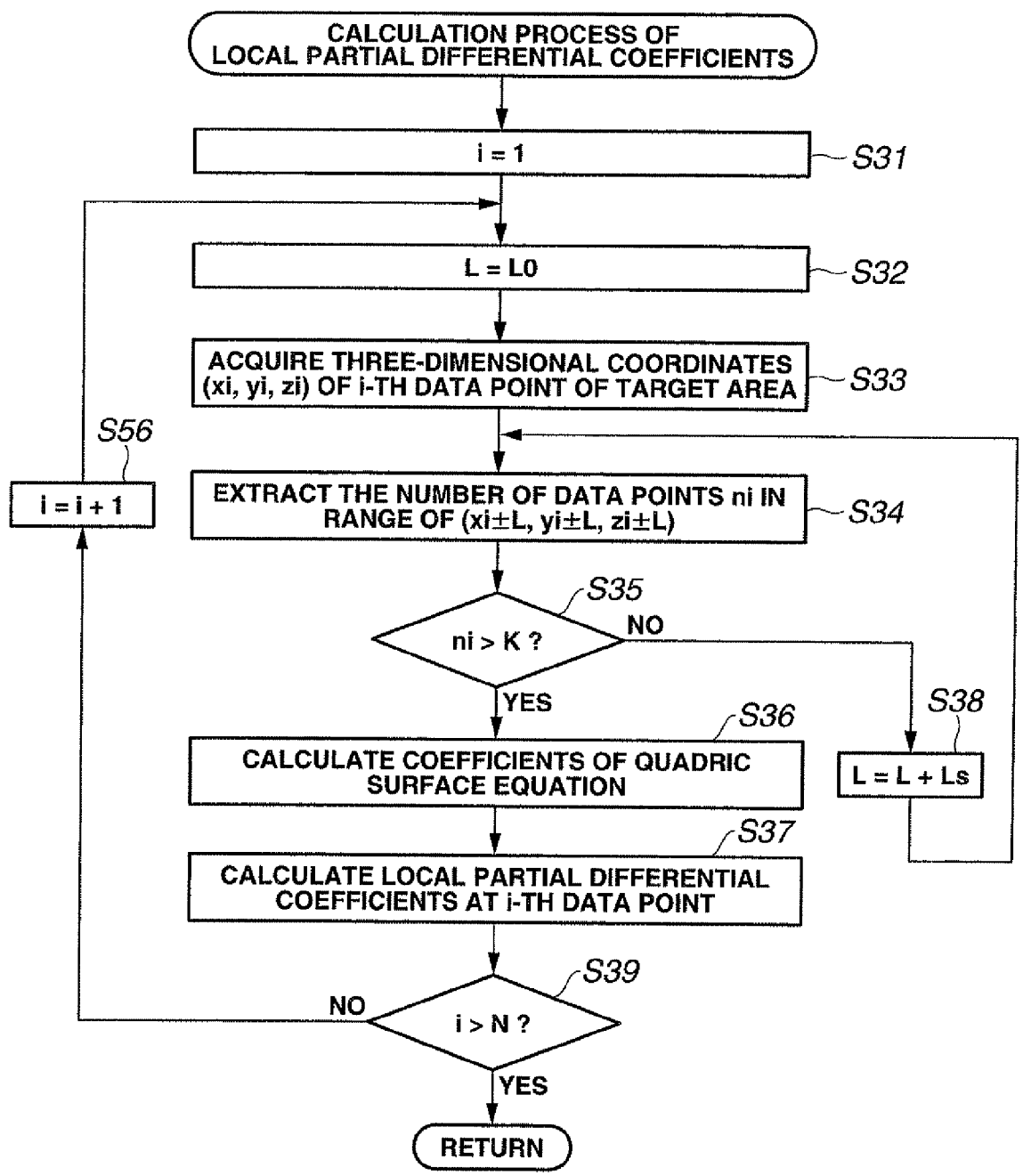
FIG. 13 is a flow chart showing a flow of the calculation process of the local partial differential coefficients of FIG. 12.
Figures 14, 15:
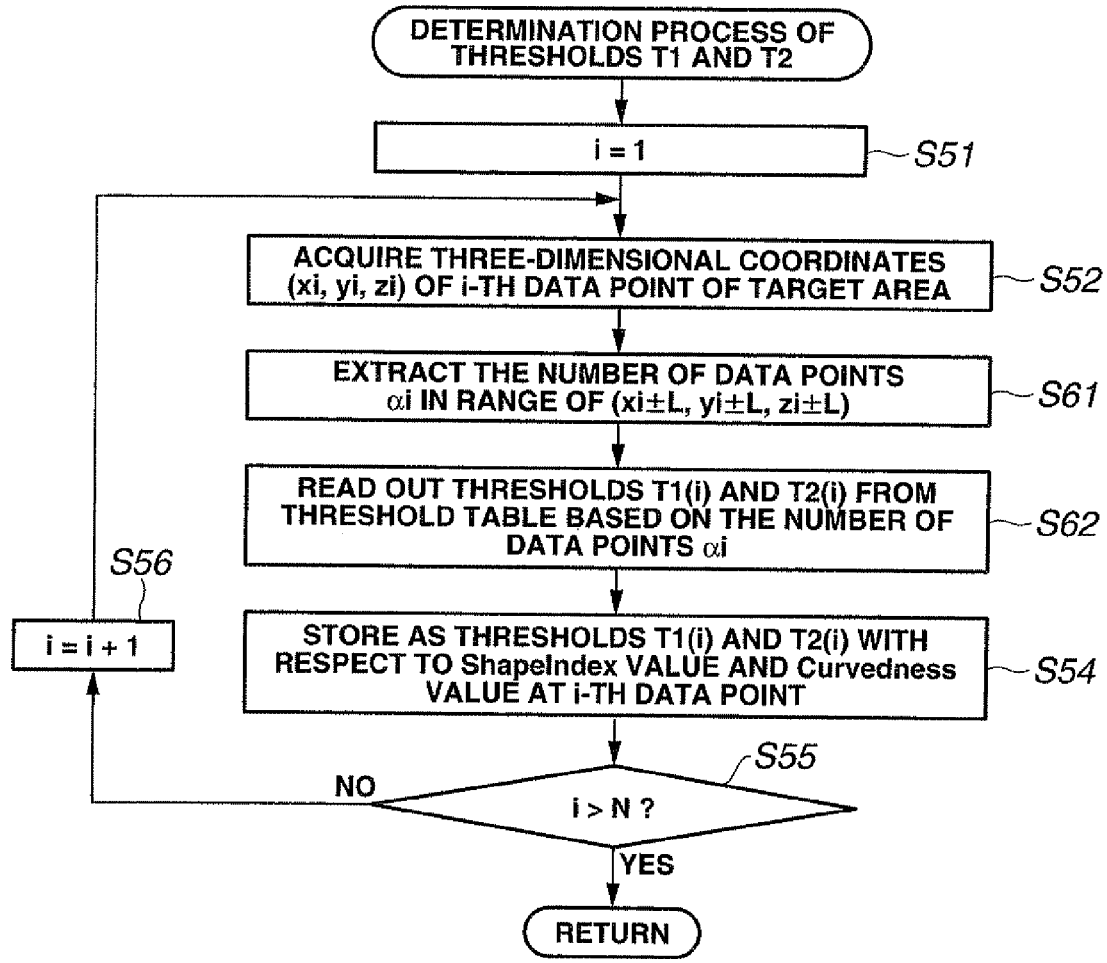
FIG. 14 is a flow chart showing a flow of the determination process of the thresholds T1 and T2 in the post-stage of the process of FIG. 13.
FIG. 15 is a diagram showing a threshold table showing a correspondence between the number of data points Mi used in the process of FIG. 13 and the thresholds T1 and T2.
Figure 16:
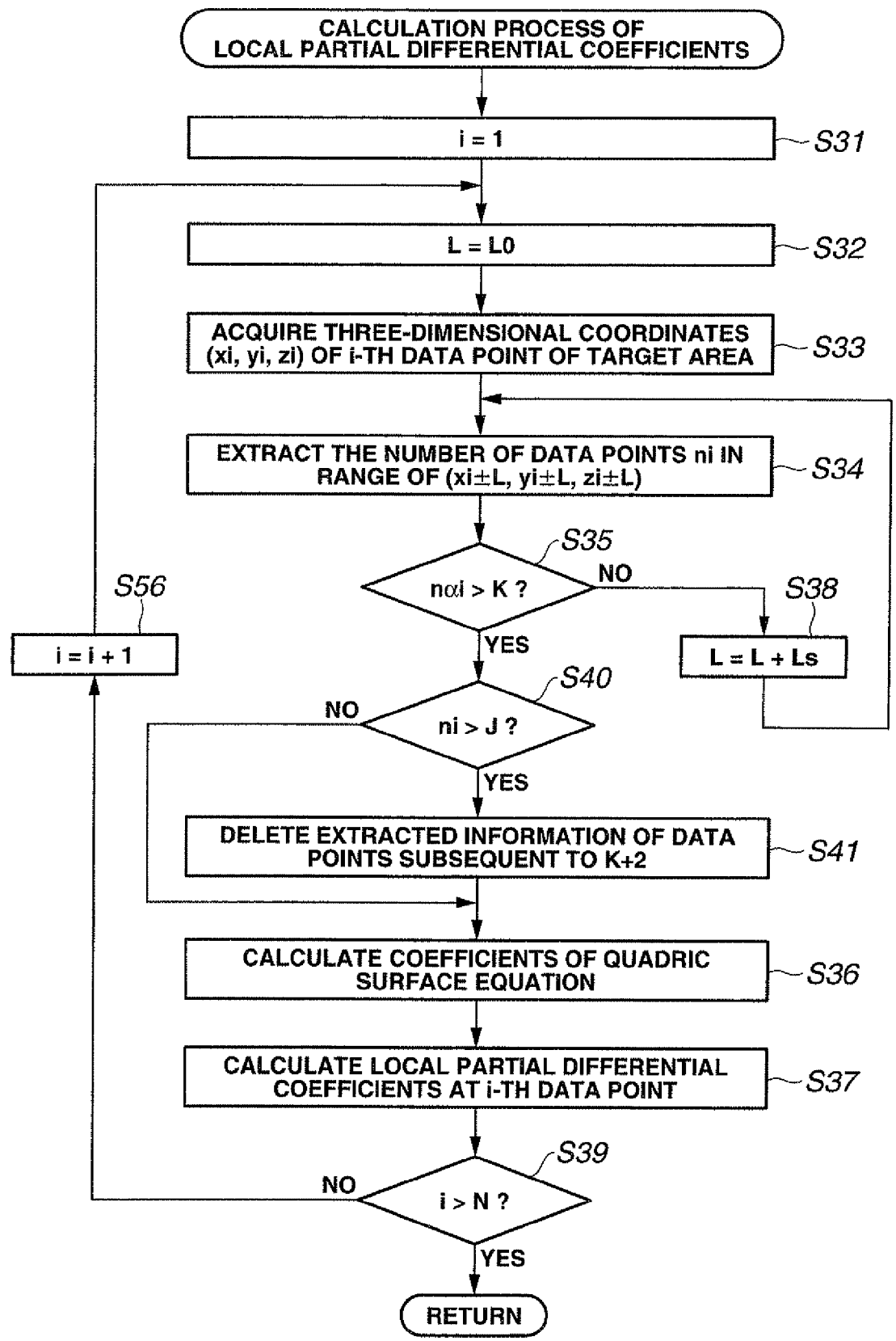
FIG. 16 is a flow chart showing a flow of a modified example of the calculation process of the local partial differential coefficients of FIG. 12.

FIGS. 12 to 16 relate to a third embodiment of the present invention. FIG. 12 is a diagram for explaining a calculation process of the local partial differential coefficients. FIG. 13 is a flow chart showing a flow of the calculation process of the local partial differential coefficients of FIG. 12. FIG. 14 is a flow chart showing a flow of the determination process of the thresholds T1 and T2 in the post-stage of the process of FIG. 13. FIG. 15 is a diagram showing a threshold table showing a correspondence between the number of data points Mi used in the process of FIG. 13 and the thresholds T1 and T2. FIG. 16 is a flow chart showing a flow of a modified example of the calculation process of the local partial differential coefficients of FIG. 13.

In the third embodiment, the calculation process of the local partial differential coefficients (step S3 of FIG. 3) and the determination process of the thresholds T1 and T2 for comparison with the values of the Shape Index value and the Curvedness value (step S5 of FIG. 3) are different from the first embodiment, and the configuration is the same as the first embodiment. Therefore only the different point will be described.

In the first embodiment, three-dimensional data points existing in the range of a fixed sized cube or sphere are used. Therefore, as shown in FIG. 12, since sparsity and density of the three-dimensional points occur in the calculation process of the local partial differential coefficients (step S3 of FIG. 3) applied in the first embodiment, a standard error of estimated local partial differential coefficients becomes large if the data is sparse. If the thresholds are set to Threshold-D based on the range where the data is dense, dropping occurs in the range where the data is sparse. If the thresholds are set to Threshold-S based on the range where the data is sparse, false detections increase in the range where the data is dense.

The calculation process of the local partial differential coefficients of the present embodiment is different from the first embodiment in that a process for determining a three-dimensional data point acquisition area is added.

In the calculation process of the local partial differential coefficients of the present embodiment, coefficients of a quadric surface equation of the intestinal tract surface at the location of one targeted point among the points on the intestinal tract surface calculated in step S2 of FIG. 3 are estimated and calculated, and the quadric surface equation is partially differentiated to obtain the local partial differential coefficients. The quadric surface equation is obtained by setting a cubic or spherical local area centering on the one targeted point, creating a matrix from coordinate values of the three-dimensional data points existing in the local area and including the one targeted point (coordinate values of 9 or more points are required), and generating a pseudo inverse matrix of the matrix.

Specifically, in the calculation process of the local partial differential coefficients of the present embodiment, as shown in FIG. 13, the shape feature value calculating unit 22c of the CPU 22 sets the parameter i to 1 in step S31 and sets an initial value L0 to a variable L when calculating the local partial differential coefficients of i-th three-dimensional data point in step S32.

Subsequently, in step S33, the shape feature value calculating unit 22c of the CPU 22 acquires three-dimensional coordinates (xi, yi, zi) of i-th data point in the target area of the three-dimensional model from the analysis information storing unit 25.

In step S34, the shape feature value calculating unit 22c of the CPU 22 acquires data point information existing in the range of a cubic range (xi±L, yi±L zi±L) centering on the coordinates (xi, yi, zi) of i-th data point from the three-dimensional data point sequences that are stored in the hard disk 27 and that indicates the intestinal tract surface. The number ni of the data point information is counted.

In step S35, the shape feature value calculating unit 22c of the CPU 22 compares the counted number ni and a predetermined value K, and if the counted number ni is greater than K, performs a coefficient calculation process of a quadric surface equation in step S36, performs a calculation process of the local partial differential coefficients in step S37, and proceeds to the calculation process of the Shape Index/Curvedness of step S4 of FIG. 3.

If the counted number ni is equal to or smaller than the predetermined value K, a predetermined increment LS is added to L in step S38 to expand the range, the process returns to step S34, and the data point information within the range is recounted.

In step S39, the shape feature value calculating unit 22c of the CPU 22 determines whether the parameter i has reached the number N of all data points in the target area of the three-dimensional model, and if not i>N, increments the parameter i in step S56 and returns to step S32. In step S39, the shape feature value calculating unit 22c of the CPU 22 repeats the processes of S32 to S39 and S56 of FIG. 13 described above until the coefficient calculation of the quadric surface equation and the calculation of the local partial differential coefficients of all data points in the target area of the three-dimensional model are completed.

According to the above processes, the size of the local area is changed such that the number of the three-dimensional data points included in the local area becomes equal to or greater than a predetermined number.

In the determination process of the thresholds T1 and T2 for comparison with the values of the Shape Index value and the Curvedness value of the present embodiment, as shown in FIG. 14, the threshold determining unit 22e of the CPU 22 sets the parameter i to 1 in step S51 and acquires, in step S52, three-dimensional coordinates (xi, yi, zi) of i-th data point in the target area of the three-dimensional model from the analysis information storing unit 25.

In step S61, the threshold determining unit 22e of the CPU 22 uses the predetermined value L to set a cubic area centering on the three-dimensional coordinates (xi, yi, zi). Thus, {(xi', yi', zi')|xi−L≦xi'≦xi+L, yi−L≦yi'≦yi+L, zi−L≦zi'≦zi+L} is set. The number of data points Mi in the cubic area is counted based on the three-dimensional data point sequences stored in the hard disk 27.

A threshold table shown in FIG. 15, in which the number of data points Mi and thresholds T1 and T2 correspond, is stored in the hard disk 27.

In step S62, based on the number of data points Mi, the threshold determining unit 22e of the CPU 22 acquires the thresholds T1 and T2 corresponding to the number of data points Mi from the threshold table.

Subsequently, in step S54, the threshold determining unit 22e of the CPU 22 stores them as thresholds $T1(i)$ and $T2(i)$ of the Shape Index value and the Curvedness value of i-th data point in the analysis information storing unit 25.

In step S55, the threshold determining unit 22e of the CPU 22 determines whether the parameter i has reached the number N of all data points in the target area of the three-dimensional model, and if not i>N, increments the parameter i in step S56 and returns to step S52. In step S55, the threshold determining unit 22e of the CPU 22 repeats the processes of steps S52, S61, S62, and S54 to S56 of FIG. 14 described above until the thresholds $T1(i)$ and $T2(i)$ are determined in all data points in the target area of the three-dimensional model.

Since the threshold process is invalid if the number of data points Mi is 0 to 8, a value 0 indicative of the invalidity is assigned to the thresholds T1 and T2. Although the number of data points in the cubic area centering on the coordinates is counted, a condition of $xk'^2+yk'^2+zk'^2<L$ may be added to count the number of data points in the spherical area centering on the coordinates.

As described, in the present embodiment, the size of the local area is changed such that the number of three-dimensional data points included in the local area becomes equal to or greater than a predetermined number, and the thresholds T1 and T2 for obtaining the three-dimensional feature values (Shape Index value and Curvedness value) are set in accordance with the point density of the three-dimensional data. Therefore, changing the process parameters in the polyp detection process in accordance with the density of the three-dimensional data enables to improve the detection accuracy of the possible polyp and to promote the improvement of the possible polyp detection rate in colon endoscopy.

If the number of data points existing in the area is too large, the process time of the coefficient calculation of the quadric surface equation increases.

Thus, as shown in a process flow of FIG. 16 as a modified example of the calculation process of the local partial differential coefficients of the present embodiment, the shape feature value calculating unit 22c of the CPU 22 may be configured to determine whether the acquired number of data points is greater than a predetermined value J (K<J) in step S40, and if greater, may limit the data points used in the coefficient calculation of the quadric surface equation to K+1 in step S41.

In this case, if the counted number ni is greater than J as a result of the comparison between the acquired number of data points and the predetermined value J, data subsequent to K+2 in the data point information is deleted, and the coefficients of the quadric surface equation are calculated.

The present invention is not limited to the above described embodiments. various changes and modifications can be made without departing from the scope of the present invention.

What is claimed is:
1. A medical image processing apparatus comprising:
a three-dimensional model estimating unit for estimating a three-dimensional model of a living tissue based on a two-dimensional image of an image of the living tissue in a body cavity, the two-dimensional image inputted from a medical image pickup apparatus;
a detection target area setting unit for setting a detection target area of a lesion with elevated shape in the three-dimensional model;
a shape feature value calculating unit for calculating shape feature values indicative of a state of the shape at each data point included in the detection target area;

a three-dimensional shape detecting unit for detecting a lesion area with locally elevated shape existing in the detection target area based on a threshold process with respect to the shape feature values; and a threshold determining unit for determining thresholds applied in the three-dimensional shape detecting unit, wherein the threshold determining unit determines the thresholds applied in the three-dimensional shape detecting unit based on coordinates in an axial direction perpendicular to the two-dimensional image of the detection target area.

2. The medical image processing apparatus according claim 1, wherein the shape feature values are a Shape Index value and a Curvedness value, and the thresholds are comparison thresholds for comparison with the Shape Index value and the Curvedness value.

3. A medical image processing apparatus comprising:

a three-dimensional model estimating unit for estimating a three-dimensional model of a living tissue based on a two-dimensional image of an image of the living tissue in a body cavity, the two-dimensional image inputted from a medical image pickup apparatus;

a detection target area setting unit for setting a detection target area of a lesion with elevated shape in the three-dimensional model;

a shape feature value calculating unit for calculating shape feature values indicative of a state of the shape at each data point included in the detection target area;

a three-dimensional shape detecting unit for detecting a lesion area with locally elevated shape existing in the detection target area based on a threshold process with respect to the shape feature values; and a threshold determining unit for determining thresholds applied in the three-dimensional shape detecting unit, wherein the threshold determining unit determines the thresholds applied in the three-dimensional shape detecting unit based on an angle formed by a visual line vector from a viewpoint to a target point and a normal vector in the detection target area of the target point, the viewpoint being an image pickup position of the two-dimensional image of the image of the living tissue in the body cavity inputted from the medical image pickup apparatus, the target point being a point on the detection target area.

4. The medical image processing apparatus according claim 3, wherein the shape feature values are a Shape Index value and a Curvedness value, and the thresholds are comparison thresholds for comparison with the Shape Index value and the Curvedness value.

5. A medical image processing apparatus comprising:

a three-dimensional model estimating unit for estimating a three-dimensional model of a living tissue based on a two-dimensional image of an image of the living tissue in a body cavity, the two-dimensional image inputted from a medical image pickup apparatus;

a detection target area setting unit for setting a detection target area of a lesion with elevated shape in the three-dimensional model;

a shape feature value calculating unit for calculating shape feature values indicative of a state of the shape at each data point included in the detection target area;

a three-dimensional shape detecting unit for detecting a lesion area with locally elevated shape existing in the detection target area based on a threshold process with respect to the shape feature values; and a threshold determining unit for determining thresholds applied in the three-dimensional shape detecting unit, wherein the shape feature value calculating unit calculates the shape feature values based on a data density distribution of each data point included in the detection target area, and the threshold determining unit determines the thresholds applied in the three-dimensional shape detecting unit based on the data density distribution.

6. The medical image processing apparatus according claim 5, wherein the shape feature values are a Shape Index value and a Curvedness value, and the thresholds are comparison thresholds for comparison with the Shape Index value and the Curvedness value.

7. A medical image processing method comprising:

a three-dimensional model estimating step for estimating a three-dimensional model of a living tissue based on a two-dimensional image of an image of the living tissue in a body cavity, the two-dimensional image inputted from a medical image pickup apparatus;

a detection target area setting step for setting a detection target area of a lesion with elevated shape in the three-dimensional model;

a shape feature value calculating step for calculating shape feature values indicative of a state of the shape at each data point included in the detection target area;

a three-dimensional shape detecting step for detecting a lesion area with locally elevated shape existing in the detection target area based on a threshold process with respect to the shape feature values; and a threshold determining step for determining thresholds applied in the three-dimensional shape detecting step, wherein the threshold determining step determines the thresholds applied in the three-dimensional shape detecting step based on coordinates in an axial direction perpendicular to the two-dimensional image of the detection target area.

8. The medical image processing method according to claim 7, wherein the shape feature values are a Shape Index value and a Curvedness value, and the thresholds are comparison thresholds for comparison with the Shape Index value and the Curvedness value.

9. A medical image processing method comprising:

a three-dimensional model estimating step for estimating a three-dimensional model of a living tissue based on a two-dimensional image of an image of the living tissue in a body cavity, the two-dimensional image inputted from a medical image pickup apparatus;

a detection target area setting step for setting a detection target area of a lesion with elevated shape in the three-dimensional model;

a shape feature value calculating step for calculating shape feature values indicative of a state of the shape at each data point included in the detection target area;

a three-dimensional shape detecting step for detecting a lesion area with locally elevated shape existing in the detection target area based on a threshold process with respect to the shape feature values; and a threshold determining step for determining thresholds applied in the three-dimensional shape detecting step, wherein the threshold determining step determines the thresholds applied in the three-dimensional shape detecting step based on an angle formed by a visual line vector from a viewpoint to a target point and a normal vector in the detection target area of the target point, the viewpoint being an image pickup position of the two-dimensional image of the image of the living tissue in the body cavity inputted from the medical image pickup apparatus, the target point being a point on the detection target area.

10. The medical image processing method according to claim 9, wherein
the shape feature values are a Shape Index value and a Curvedness value, and the thresholds are comparison thresholds for comparison with the Shape Index value and the Curvedness value.

11. A medical image processing method comprising:
a three-dimensional model estimating step for estimating a three-dimensional model of a living tissue based on a two-dimensional image of an image of the living tissue in a body cavity, the two-dimensional image inputted from a medical image pickup apparatus;
a detection target area setting step for setting a detection target area of a lesion with elevated shape in the three-dimensional model;
a shape feature value calculating step for calculating shape feature values indicative of a state of the shape at each data point included in the detection target area;
a three-dimensional shape detecting step for detecting a lesion area with locally elevated shape existing in the detection target area based on a threshold process with respect to the shape feature values; and
a threshold determining step for determining thresholds applied in the three-dimensional shape detecting step, wherein
the shape feature value calculating step calculates the shape feature values based on a data density distribution of each data point included in the detection target area, and
the threshold determining step determines the thresholds applied in the three-dimensional shape detecting step based on the data density distribution.

12. The medical image processing method according to claim 11, wherein
the shape feature values are a Shape Index value and a Curvedness value, and the thresholds are comparison thresholds for comparison with the Shape Index value and the Curvedness value.

* * * * *